(12) United States Patent
Boschetti Sacco et al.

(10) Patent No.: US 10,201,308 B2
(45) Date of Patent: Feb. 12, 2019

(54) PORTABLE DEVICE FOR MONITORING AND REPORTING OF MEDICAL INFORMATION FOR THE EVIDENCE-BASED MANAGEMENT OF PATIENTS WITH CHRONIC RESPIRATORY DISEASE

(75) Inventors: Paolo Boschetti Sacco, Rome (IT); Cesare Saltini, Rome (IT); Luigino Calzetta, Rome (IT)

(73) Assignee: MIR SRL-MEDICAL INTERNATIONAL RESEARCH, Rome (IT)

( * ) Notice: Subject to any disclaimer, the term of this patent is extended or adjusted under 35 U.S.C. 154(b) by 1559 days.

(21) Appl. No.: 13/814,824

(22) PCT Filed: Aug. 9, 2010

(86) PCT No.: PCT/IT2010/000361
§ 371 (c)(1),
(2), (4) Date: Apr. 3, 2013

(87) PCT Pub. No.: WO2012/020433
PCT Pub. Date: Feb. 16, 2012

(65) Prior Publication Data
US 2013/0184540 A1    Jul. 18, 2013

(51) Int. Cl.
*A61B 5/00* (2006.01)
*A61B 5/087* (2006.01)
(Continued)

(52) U.S. Cl.
CPC ............ *A61B 5/4884* (2013.01); *A61B 5/087* (2013.01); *A61B 5/1118* (2013.01);
(Continued)

(58) Field of Classification Search
CPC ...... A61B 5/4884; A61B 5/087; A61B 5/1118; A61B 5/14551; A61B 2560/0431; G06F 19/3418
(Continued)

(56) References Cited

U.S. PATENT DOCUMENTS 5,865,736 A * 2/1999 Baker, Jr. ............ A61B 5/02455
600/323
6,416,471 B1 * 7/2002 Kumar .................. G06F 19/323
128/903
(Continued)

FOREIGN PATENT DOCUMENTS

WO    2007/071180 A1    6/2007

OTHER PUBLICATIONS

Hatem Alameri et al.: "Submaximal exercise in patients with severe obstructive sleep apnea", Sleep and Breathing ; International Journal of the Science and Practice of Sleep Medicine, Springer, Berlin, DE, vol. 14, No. 2, Sep. 25, 2009 (Sep. 25, 2009), pp. 145-151, XP019833400, ISSN: 1522-1709 abstract; tables 2-3 section Material and methods.
(Continued)

*Primary Examiner* — Christopher A Flory
*Assistant Examiner* — Vynn Huh
(74) *Attorney, Agent, or Firm* — Young & Thompson

(57) ABSTRACT

An integrated tele-health system/device for monitoring and reporting medical information for the evidence-based management of patients with chronic respiratory disease. The device includes a central unit which measures and collects information related to the state of health of the patient, and is provided with elements for wireless or cable transmission of the collected data using a microprocessor based system with a touch screen display, USB communication port and Bluetooth. The device further includes: a removable sensor
(Continued)

for the measurement of respiratory air flow and volume, a removable pulse oximetry sensor and a motion sensor. Stored data can be then delivered through landline, broadband, wireless and cell-phone technology to be received by a web server and can then be accessed by medical staff. Being completely portable, the device is provided with a battery of known type, which can be substituted by the user or can be rechargeable.

14 Claims, 3 Drawing Sheets

(51) Int. Cl.
  *A61B 5/11* (2006.01)
  *A61B 5/1455* (2006.01)
  *G06F 19/00* (2018.01)
(52) U.S. Cl.
  CPC .......... *A61B 5/14551* (2013.01); *G06F 19/00* (2013.01); *G06F 19/3418* (2013.01); *A61B 2560/0431* (2013.01)

(58) Field of Classification Search
  USPC .................................................. 600/300, 301
  See application file for complete search history.

(56) References Cited

U.S. PATENT DOCUMENTS

| | | | |
|---|---|---|---|
| 6,712,762 | B1 | 3/2004 | Lichter et al. |
| 6,790,178 | B1 | 9/2004 | Mault et al. |
| 2006/0173257 | A1* | 8/2006 | Nagai .................. A61B 5/1135 600/323 |
| 2006/0217603 | A1 | 9/2006 | Nagai et al. |
| 2010/0083968 | A1* | 4/2010 | Wondka ............. A61M 16/125 128/204.23 |
| 2012/0101411 | A1* | 4/2012 | Hausdorff ............ A61B 5/1117 600/595 |

OTHER PUBLICATIONS

International Search Report, dated May 20, 2011, from corresponding PCT application.

* cited by examiner

PORTABLE DEVICE FOR MONITORING AND REPORTING OF MEDICAL INFORMATION FOR THE EVIDENCE-BASED MANAGEMENT OF PATIENTS WITH CHRONIC RESPIRATORY DISEASE

BACKGROUND OF THE INVENTION

Field of the Invention

The present invention relates to an integrated tele-health system/device for the monitoring and reporting of medical information for the evidence-based management of patients with chronic respiratory disease.

INTRODUCTION

Description of the Related Art

At the base of the new requirements for better and more intelligent treatments must be a series of evidence-based management tools to help to create a more rational and intelligent way to deal with health based on evidence.

Scientific, economic, cultural and social progress have combined to help us obtain significant advantages in health management. The average life expectancy of the population has increased over the last ten years. The conditions which society must come to terms with are those chronic degenerative diseases, which although they cannot be cured, can be kept under control with suitable pharmaceutical and behavioural therapies.

The respiratory pathologies are at the current state of play one of the most significant health problems for the number of patients afflicted—even younger people—as well as for the high rate of mortality and the prevalence, and the significantly disabilitating effects on the patients and for the very high direct and indirect costs associated.

According to the American Thoracic Society (ATS) and the European Respiratory Society (ERS) "chronic obstructive pulmonary disease (COPD) affects about 210 million people globally and causes some 3 million deaths annually. The disease is a major drain on healthcare budgets with 50% of costs accounted for by hospital admissions, much of which could be avoided through development of more responsive models of care that allow earlier recognition and treatment of exacerbations".

An exacerbation can be defined as a sustained worsening of the patient's symptoms from that beyond normal day-to-day variation. Exacerbations can result in a more rapid decline of lung function, increased peripheral muscle weakness, decreased quality of life, increased health care costs, and increased mortality. It has been demonstrated that early therapy speeds exacerbation recovery, and reduces health care utilization. Patients should be instructed to respond early in the course of an exacerbation by activating their predetermined action plan.

In a self-management program, well-designed clinical trials that provide valid, reproducible and interpretable results should also instruct the patient to treat and prevent the onset of respiratory exacerbations.

Real-time patient remote monitoring and screening for homecare purposes can be delivered through landline, broadband, wireless and cell-phone technology. These tele-health applications may forever change, while dramatically improving the way healthcare will reach the ever increasing number of COPD patients worldwide.

Chronic respiratory diseases can lead to chronic respiratory failure: inadequate gas exchange by the respiratory system, with the result that arterial oxygen and/or carbon dioxide levels cannot be maintained within their normal ranges. When chronic respiratory failure occurs, there is an increase in the impact of the disease on the patient's daily life and well-being.

Lifestyle, which includes physical inactivity in daily life, plays a very important role in terms, of both disability and mortality. It is now well recognized that regular physical activity may prevent or delay the onset or progress of different chronic diseases. It is known, for instance, that in patients with chronic obstructive pulmonary disease (COPD), lower levels of physical activity in daily life are related to higher risk of hospital readmission and also to shorter survival.

One of the main consequences of chronic respiratory disease is a daily activity performance drop, which must be measured in this patient population. Therefore, the assessment of the amount and intensity of physical activity in daily life is of major importance given the close relationship between activity levels and health.

SUMMARY OF THE INVENTION

The device comprises, substantially a central unit which measures and collects information related to the state of health of the patient, and it is provided with means for wireless or cable transmission of the collected data using a microprocessor based system with a touch screen display, USB communication port and Bluetooth. According to the invention, the device further comprises: a removable sensor for the measurement of respiratory air flow and volume, a removable pulse oximetry sensor and a motion sensor. Stored data can be then, delivered through landline, broadband, wireless and cell-phone technology to be received by a web server and can then be accessed by medical staff.

Being completely portable, the device according to the invention is provided with a battery of known type, which can be substituted by the' user or it can be rechargeable.

BRIEF DESCRIPTION OF THE DRAWING FIGS

A better understanding of the present invention will be obtained with reference to the following description and with reference to the attached plates of drawings, which illustrate merely by way of non-limiting example a preferred embodiment thereof:

DESCRIPTION OF THE INVENTION

Figure 1:
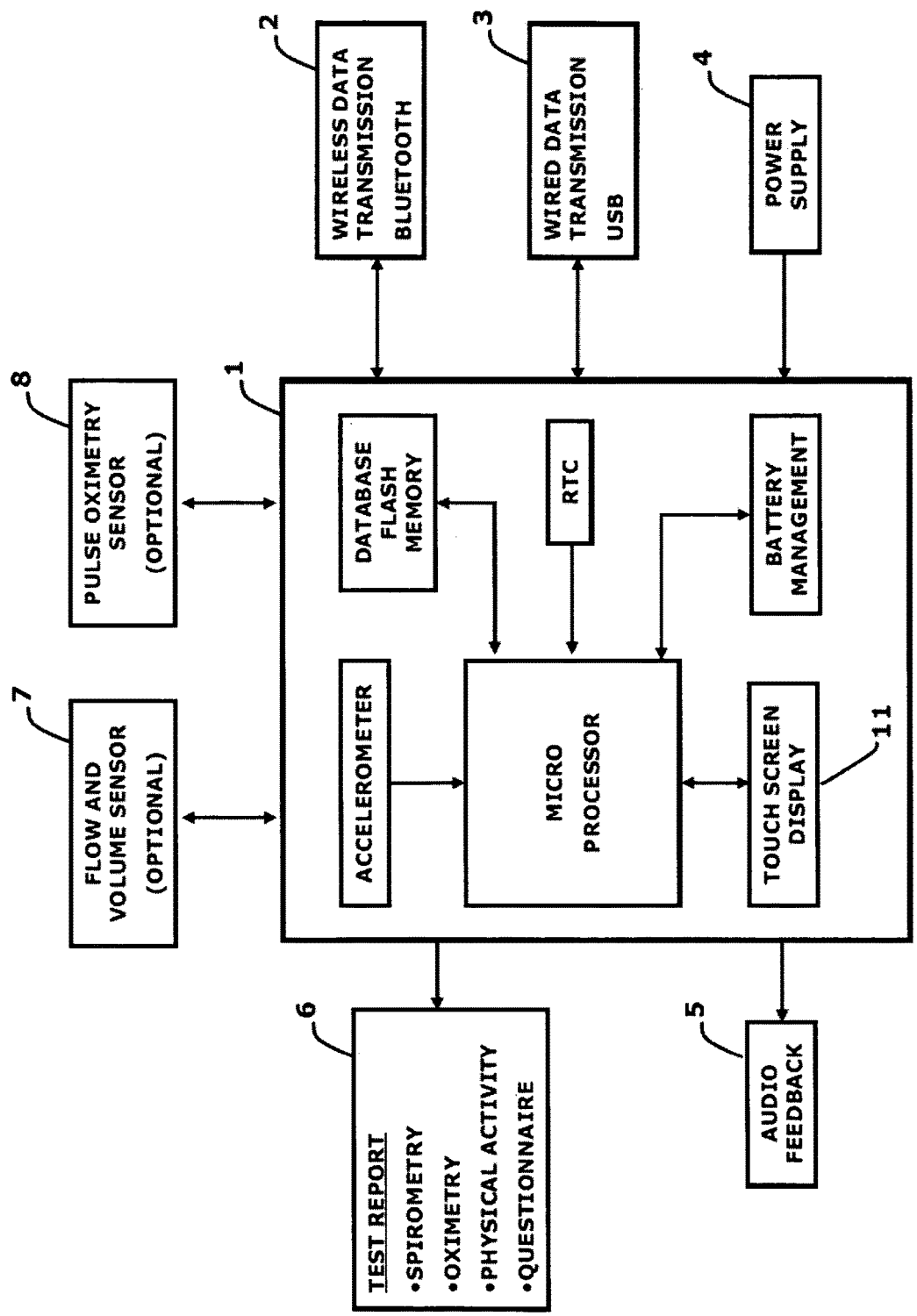
FIG. 1 is a block diagram of the device according to the present invention.
Figure 2:
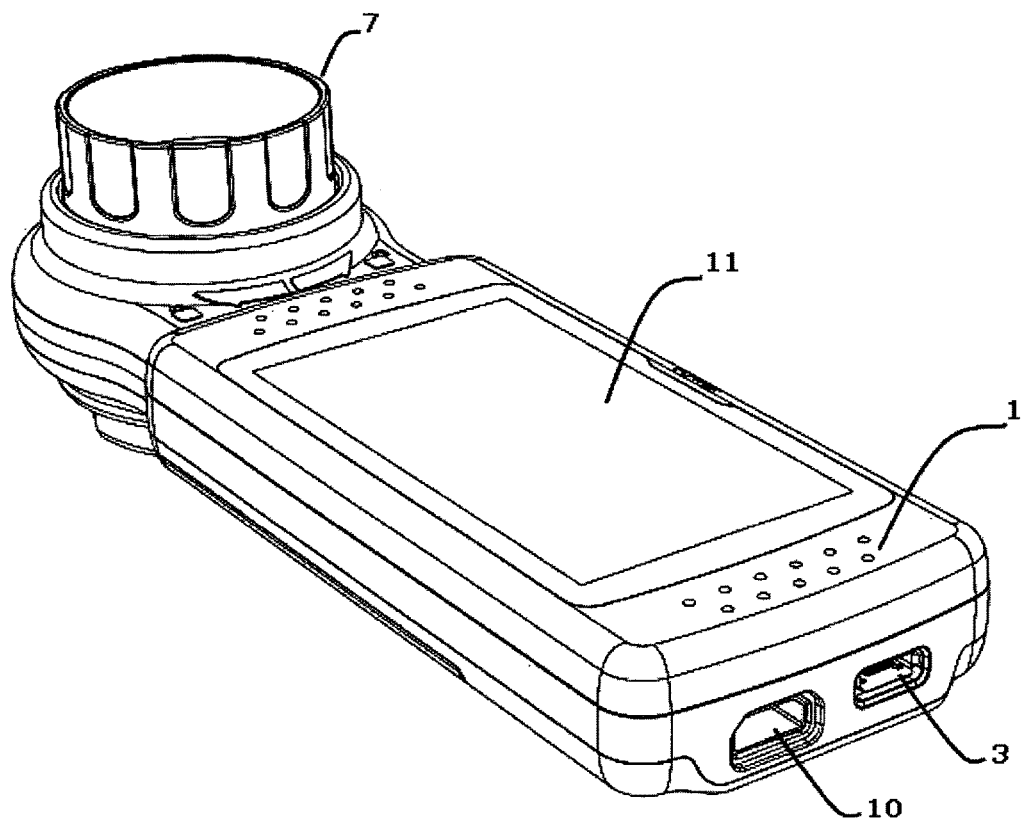
FIG. 2 shows a preferred embodiment of the device with flow and volume sensor connected.
Figure 3:
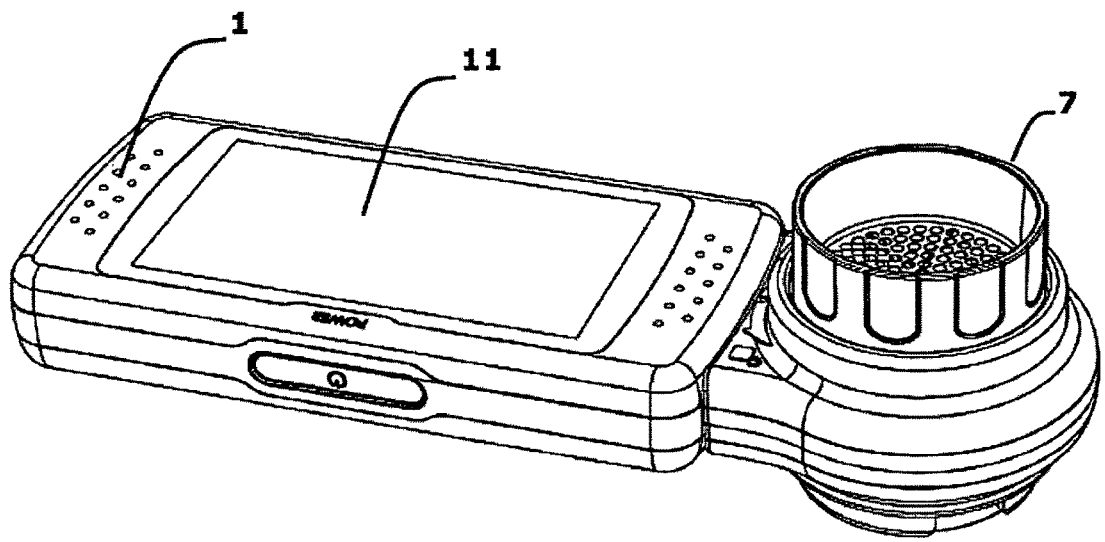
FIG. 3 is a different view corresponding to FIG. 2.

In view of the above, it appears clear that the state of health of a patient affected by respiratory disease like COPD requires a daily "overview" of several vital signs (or vital parameters) in order to spot in advance any potential worsening of the condition which, if not brought under control, generally leads to exacerbations and eventually to a spell in hospital.

The present invention is specifically aimed to provide a device and/or system for carry out said "overview" directly by the patient him/herself.

Often these patients are able to monitor several vital signs at home, for instance pulse oximetry, which with respect to the patients baseline resting value can be subject to a fall off under exercise or during sleep, when the spontaneous ventilation reduces for physiological reasons.

Pulse oximetry is the most simple, non-invasive method for evaluating the level of oxygen in the blood. This measurement provides a parameter called oxygen saturation (% $SpO_2$), closely related to $SaO_2$ measured by blood sampling, a much more complicated and invasive method. There isn't life without oxygen: this is why pulse oximetry is considered a vital sign.

In the past few years through technological progress, which has enabled the production of pocket-size pulse oximeters and spirometers at reduced costs, many doctors have included the measurement of % $SpO_2$ and expiratory peak flow (PEF) as vital signs equally as important as the standard ones (such as body temperature, heart rate, blood pressure), used when performing a general medical check-up of a patient to identify the type of disorder present.

Performance Evaluation

A fundamental objective in the management of respiratory disease is to increase a patient's performance in routine daily activities. Performance assessment is possible by either patient reporting or by direct observation by noting the rate, speed or efficiency of a particular activity. However this impractical process is difficult to standardize and extremely time consuming.

According to the present invention, it is provided a device comprising motion detectors and activity monitors that allow for a plausible daily activity evaluation in any setting.

The precise quantification of physical activity is of particular importance in measuring the outcomes of interventions in frail, sedentary populations such as COPD and the elderly, because even small improvements in physical functioning such as walking and balance may translate into significantly improved quality of life.

Objective assessment of daily activity performance in non laboratory-settings is becoming a reality thanks to activity monitors in the form of a simple pedometer which counts the number of steps taken by a patient to more elaborate devices capable of measuring movement on three axis.

An accelerometer is a technologically very advanced device, which allow the quantity and intensity of movements to be determined and measured. The instrument is able to measure both the total amount and the intensity of spontaneous activities performed throughout the day in the subject's own environment.

Walking is now considered as the most important and common type of physical activity performed in daily life and is the activity targeted for improvement in most pulmonary rehabilitation programs. Walking more in daily life is an important indicator of improvement after respiratory rehabilitation protocols, and this walking can indeed be accurately assessed by motion sensors. Some tests can be self-paced such as the 6-minute walk test (6MWT), and require no advanced training or special equipment. The 6MWT is a very simple, safe and reproducible fitness test, and it is widely used in the evaluation of respiratory diseases. The test requires no complex instrumentation, can be made easily even by patients with a severe level of disability and, last but not least, represents more closely than any other test "normal life activity" and so is therefore an excellent indicator of the quality of life of the patient.

Guidelines for the application of the 6MWT in a clinical setting were developed by the American Thoracic Society (ATS) in 2002. The standard procedure requires that at the start of the test and then at every one minute interval during the test, a pulse oximeter is used to record (a) the saturation (SpO2%) and (b) the heart rate (BPM) of the patient. In addition, at the end of the test, the total distance covered should be recorded.

People who suffer of moderately severe respiratory impairment can perform a 6MWT which has proven to be extremely useful to measure patient response to therapeutic interventions for, pulmonary and cardiac disease.

It is common practice that, in the event that the SpO2 level falls below 82% during the 6MWT, the test should be halted and then repeated with the patient given supplemental oxygen (O2).

In this case, the test in generally repeated following a rest interval of at least 15 minutes, with increasing oxygen flow of 2, 4 and then 6 liters per minute until the patient is able to complete the test maintaining an SpO2% level of at least 90% during the whole test.

According to the present invention, the mechanisms of exercise intolerance can now be studied in further depth through the acquisition of physiologic measurements such as the distance walked and the reduction of the oxygen level in the blood during the exercise.

Walking is a simple yet ideal form of daily exercise to evaluate the overall response of the pulmonary and cardio-vascular systems, systemic circulation, peripheral circulation, blood, neuromuscular units, and muscle metabolism.

Exercise testing in the routine clinical assessment of the functional status of a patient is now considered a fundamental component because health-related quality of life, survival rates and hospitalization rates are all affected by the degree of exercise tolerance impairment in COPD patients.

Calculation of the CS Index or O2_GAP for Long Term Oxygen Prescription

One of the objective of the invention is the use of the 6MWT to determine the prescription of long term oxygen. An equation which can be integrated into an electronic device, in order to calculate the oxygen requirement of the patient through a 6MWT carried out without any additional oxygen supply to the patient.

The equation was derived according to the following method. Ninety six patients with respiratory disease were required to carry out the 6MWT in ambient air and without any supplementary oxygen. The parameters of this 6MWT were recorded every minute ie the distance walked, the SpO2% from the start to the end of the test, as well as the Heart Rate, the recovery time, the degree of breathlessness and fatigue, as per the international guidelines.

Then using this data, the following parameters were derived or calculated as illustrated below.

Figure 4:
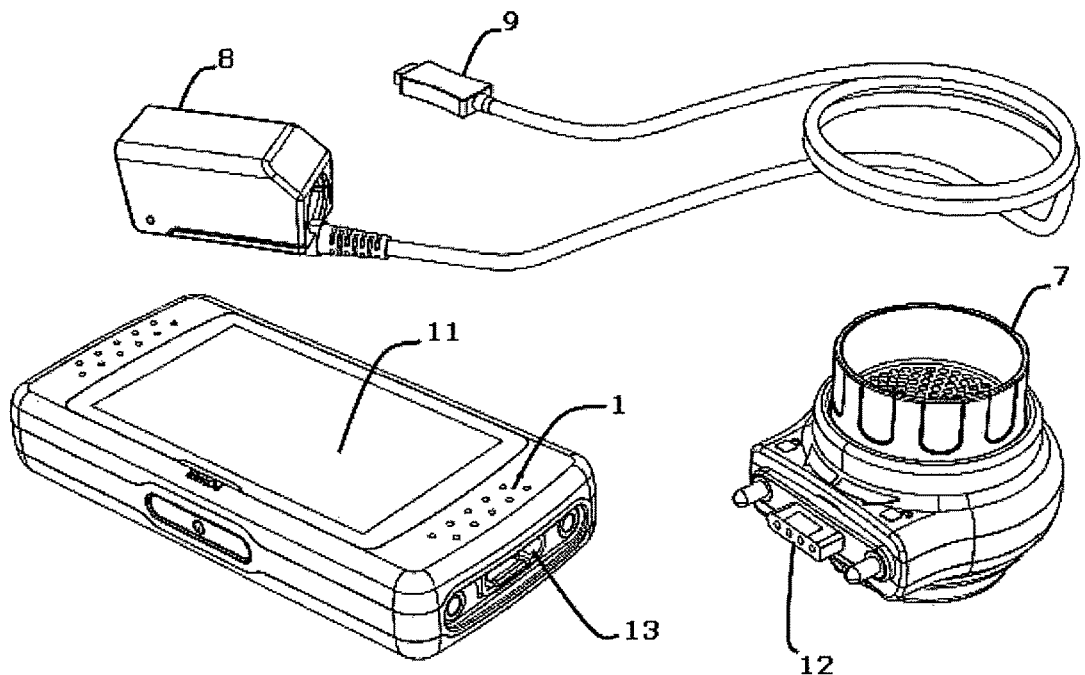
FIG. 4 shows the invention with sensors disconnected.
Figure 5:
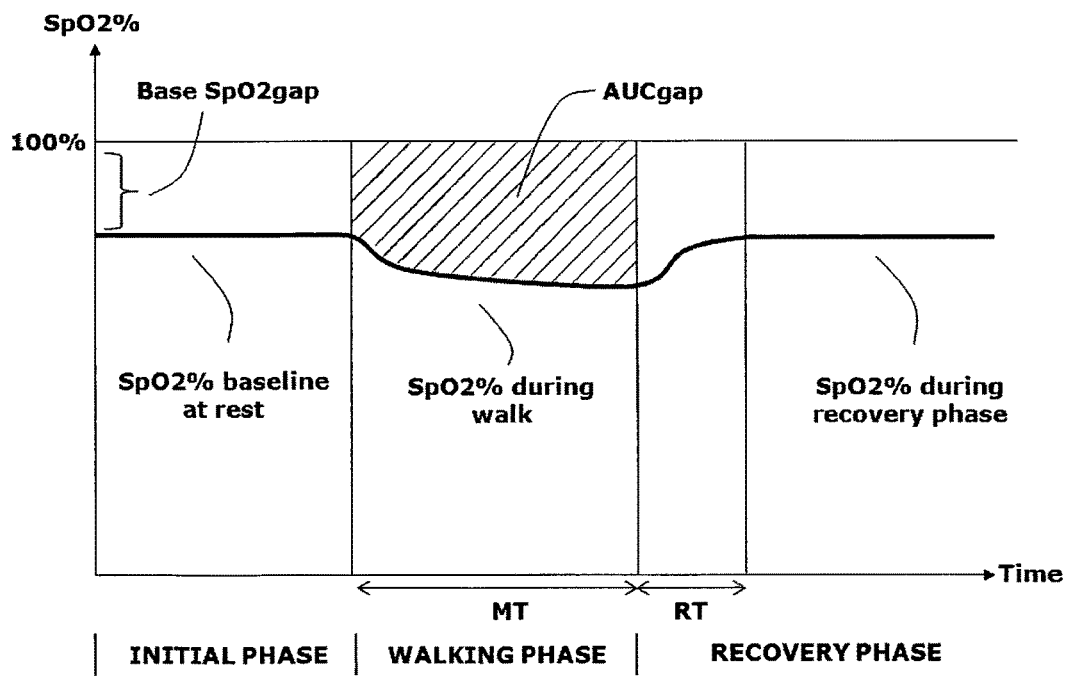
FIG. 5 is a diagram of $SpO_2$% vs time during 6MWT.

(a) AUCgap, which represents the difference between the area under the curve where SpO2%=100% vs. time and the area below the curve showing the SpO2% vs. time of the patient during the test. The time limits for the evaluation of the area are represented by the duration of walk phase (see FIG. 4).

(b) MT, which represents the test duration expressed in minutes (from a minimum of 0 to a maximum of 6).

(c) Base SpO2gap, which represents the difference between SpO2%=100% and the SpO2% baseline at rest before the start of the walk phase.

(d) RT which represents the recovery time in seconds of the patient at the end of the test, for the SpO2 value to return to the base value recorded before the test, even if the test is stopped before the full 6 minutes.

(e) PPD which represents the percent predicted distance, which is the percentage of the distance covered by the patient during the test compared to the distance covered by a normal subject. The distance (in meters) covered by a normal subject is calculated from the equation by Enright and Sherill, where:

For males: (7.57×height in, cm)−(5.02×age in years)−(1.76×weight in kg)−309

For females: (2.11×height in cm)−(5.78×age in years)−(2.29×weight in kg)−667

In the case that a patient has a base SpO2% at rest below 82% prior to the start of the test, then the patient cannot make the test without a supplement of 6 L/min of oxygen.

The equation for the calculation of the CS Index or O2_Gap, is expressed as follows:

$$\begin{cases} \text{If } MT \geq 1, \text{then:} \\ O2(L/min) = \dfrac{\left\{ \dfrac{\left[(AUCgap/MT) + (BaseSPO2gap/7)\right]^2 + \sqrt{RT}}{\sqrt{PPD}} - 9.31 \right\}}{8.94} \\ \text{If } MT = 0, \text{then:} \\ O2(L/min) = 6 \end{cases}$$

This equation enables us to calculate the O2_Gap, that we have defined also CS Index, which represents the quantity of oxygen expressed in L/min which must be given to a patient in order that the patient can complete the 6MWT without desaturating below the level of 90% SpO2, and also without desaturating below the level of 82% SpO2 for the patients who require 6 L/min of oxygen in order to complete the test.

The application of the CS Index equation in the calculation of the "oxygen gap" in the 6MWT carried out without the supply of supplemental oxygen, to calculate the oxygen requirement when the test is carried out with supplemental O2.

The capacity of the 6MWT to determine the quantity of oxygen required for the test to be carried out has been evaluated using a group of patients which included:

(a) A sub group of patients able to make the test without supplemental O2 (0 L, n=27),
(b) A sub group requiring supplemental oxygen at a flow rate of 2 L/min (2 L, n=24)
(c) A sub group requiring supplemental oxygen at a flow rate of 4 L/min (4 L, n=24)
(d) A sub group requiring supplemental oxygen at a flow rate of 6 L/min (6 L, n=21).

The application of the equation to calculate the CS Index to the analysis of the results of the 6MWT in patients within the same subgroup enables distinctions to be made between these patients.

The advantages of using the CS Index equation in clinical practice and in pulmonary/respiratory laboratories. The equation is of considerable benefit in the management of respiratory patients within pulmonary and respiratory laboratories, in the pulmonology, cardiology and rehabilitation fields as the equation, as illustrated above, enables the GAP_O2 (ie the O2 requirement to complete the test) to be determined by a single standard walking test without any supplemental oxygen. In this way, the successive tests with supplemental oxygen supplies of 2 L/min up to 6 L/min are no longer required, it is sufficient to analyse the parameters measured in the 6MWT using the new equation.

This brings both a greatly reduced level of effort and stress for the patient as well as a saving for the respiratory lab in terms of physical resources as well as trained personnel due to the reduced time required, the new total time could be even ⅛-⅒ of the time required to determine the amount of oxygen necessary.

In particular, the function obtained predicts the oxygen requirement as shown in the successive 6MWT carried out with an O2 flow from 0 to 6 L/min, showing in a statistically significant way the quantity of oxygen required to make the test without desaturating below 90% SpO2 or below 82% for the patients needing 6 L/min O2.

In conclusion, the equation calculates the size of the oxygen gap in the walking test with a high degree of sensibility, specificity and diagnostic accuracy with sensibility=91.35%, specificity=92.59% and diagnostic accuracy=91.88%, in the calculation and prediction of the O2 requirement to complete the exercise.

Quality-of-Life Measurements

Quality of life can be defined as "the gap between that which is desired in life and that which is achieved". The areas affected by health status which reflect the effect of respiratory disease on the ability to perform and enjoy daily activities are the main focus of health-related quality of life (HRQL)

Increasing documentation of the favourable effect of rehabilitation therapy for COPD patients is proof that no other therapy has the same rate of improvement in exercise endurance, dyspnea, functional capacity and overall quality of life.

According to the most recent guidelines published by the main international scientific lung societies, the assessment of patient-centered outcomes, such as symptoms, performance in daily activities, exercise capacity and health-related quality of life (HRQL), should be an integral component of pulmonary disease management. As well as the value of oxygen saturation, the management suggested by the new guide lines requires the evaluation of the improvement of the performance and of the exercise capacity, intended to mean the patient's ability to engage in activities of daily living, the measurement of the respiratory function by spirometry as well as the compilation of a specific questionnaire on the quality of life and on the symptoms.

In practice for the patient, and in particular for the older patients, it is very complex if not impossible to manage several different medical devices able to measure all of the parameters proposed by the new guide lines. In addition, it is very difficult for the patient to transfer all of the measured parameters to the medical centre.

The innovative new device/system according to the present invention, is developed to measure and to transmit all of the required diagnostic parameters for the "home care" monitoring of a patient with chronic respiratory disease. However, it has become clear that regardless of the type of respiratory disease, patients experience a substantial morbidity from secondary impairments, such as peripheral muscle, cardiac, nutritional, and psychosocial dysfunction.

This device carries out the functions required by the healthcare givers, who need to provide a better level of care based on new high technology at low cost with complete integration. The clinical application consists of non invasive and high technology testing, with low cost and easy to use instruments and sensors. The device is simple to use which is a new development for home care, where the technology has not always been simple, especially for older patients.

So the traditional concept of a visit to the doctor is extended to a virtual visit, as every patient can make use of these services even staying at home. And thus a new intelligent and completely digital ambient is created, combining diagnostic instrumentation with information technology as well as communications.

A Comparison of the Physical Activity Carried Out by a Patient

According to the latest, scientific publications in the field of pneumology, the distance walked is of fundamental importance in the evaluation of the state of health of a patient with chronic respiratory disease. In addition, when two tests by the same patient are compared, then if the trend of the desaturation (in other words the reduction of the % $SpO_2$) during the test is different, then the evaluation only of the distance walked is not sufficient.

Let us therefore define an innovative index/parameter: Desaturation Area/Movement.

This parameter represents the area under the curve, including the baseline value at rest of the % $SpO_2$ value and the graph of the % $SpO_2$ during exercise, for instance during walking, shown in relation to the total movement recorded in all three directions by the accelerometer activity during the test. This area under the curve can also be shown in relation to the movement represented by the number of steps taken, also calculated by the accelerometer.

Considering that the device according to the present invention is able to measure simultaneously the % $SpO_2$ (pulse oximetry) as well as the physical activity (accelerometry), the device is also able to calculate said index (Desaturation Area/Movement) and to show it on the display at the end of a measurement session.

This represents a peculiar feature of the invention and has a very significant implication in the evidence-based evaluation of the cardio-respiratory system during physical exercise, and thus in the evidence-informed manner. Indeed until now, as well as the difficulty of having to use two different devices, for instance a pedometer and a pulse oximeter, to measure the $SpO_2$ values and the distance walked, this index was simply not available.

The current situation gives great difficulties both to the patient seeking efficient self-management, as well as to the medical staff. Using the present invention these problems can be completely overcome.

In other words, if we consider a car which is in perfect mechanical condition, it is logical to think that this car is able to cover a greater distance with a liter of fuel compared to a car which is not in perfect mechanical condition. In the same way, a patient during physical activity will have a lesser or a greater level of fall of the % $SpO_2$ (desaturation) according to his or her state of health. The relationship between Desaturation Area and Movement indicates the level of desaturation in relation to the movement or the distance covered and can therefore be considered an index of the performance of the patient.

The Desaturation Area/Movement enables the comparison of two measurement sessions in order to measure the variation in the state of health of the patient through their own performance and exercise capacity.

Description of the Sensors

The heart of the system is the central unit which is based on microprocessor technology. The invention is also provided with input/output means by which the user interfaces with the unit. These I/O means are preferably constituted by a touch-screen display.

In a preferred embodiment, when the device is switched on, it requires the insertion of some general and some respiratory specific health-related quality of life questions. This questionnaire is first configured for the patient by the health team, who can switch on or off the various optional questions according to the specific patients requirements. Individual components of quality of life, for instance working or resting activity etc., include symptoms, functional status, mood. Questionnaires can measure these components individually or with a composite score. When the information session is completed then the patient can select the type of diagnostic test to be carried out.

One of the main advantages offered by this invention is that the central unit comprises an electrical and mechanical connection assembling system for connecting to a removable sensor for the measurement of respiratory air flow and volume. In order to allow a simpler access to the other functions the system offers, this sensor can be completely removed from the central unit when spirometry testing is not required. When the flow measurement head has been connected to the central unit through the associated conjugated connector with conjugate contact elements, spirometry tests can be carried out to determine the most important spirometry parameters such as the PEF, FEV1, FEF25%-75%. At the end of the test, the unit displays the results and compares them to the reference values which have been set by the doctor during the device setup. Thus the patient can view various messages about his/her state of health. When the test is finished the respiratory measurement head (the complete sensor) can be removed from the central unit.

The central unit can be placed within a belt worn close to the body on the waist, wrist or ankle of the patient, and then a finger probe is worn connected to the central unit for the pulse oximetry, to measure both the % $SpO_2$ and the Pulse Rate (BPM). The test can be carried out at rest, or during physical exercise or even overnight during sleep.

According to a peculiar feature of the invention, at the same time as the pulse oximetry is measured and recorded, the trixial accelerometer which is integrated into the central unit, carries out the function of activity monitor as well as motion detector.

If the patient walks then the number of paces can be detected and recorded as well as the physical activity in each of the three directions. If instead the patient sleeps then the position of the body can be recorded during sleep face up, facedown, right side or left side, etc., as well as the movements during the complete test period.

At the end of the test, any periods of arterial desaturation, will be analyzed and compared to the results of the physical activity measured by the accelerometer. Indeed, it is well known that in many cases patients with chronic respiratory conditions will have a rapid fall off in arterial oxygen saturation following exercise, even very modest exercise.

Specifically the calculation of the index Desaturation Area/Movement or the steps taken, will give very important information for each test, or on the improvement or deterioration in the respiratory condition by comparing the current test with a previous test made: this also enables effective self management by the patient who has objective data with which to compare his or her exercise tolerance and to remain within the limits suggested by the doctor.

A further and very significant advantage of the invention is the possibility to transmit the test data to a web server so that the test data can then be seen by the doctor and thus the doctor can vary the therapy as required very quickly indeed. In some cases, these patients are treated with oxygen at home in order to compensate any desaturation.

In addition, desaturation during sleep, and above all the rapid desaturation caused by sleep apnea, can be linked to a body position and the analysis of the sleeping position is possible thanks to the accelerometer within the device. Also, even minimum periods during sleeping hours when the patient stands up or walks can be identified as waking hours and thus excluded from the sleep analysis.

Further Advantages of the Invention

The subject of this invention is a new device with a specific and innovative way of use both for the patient who uses it and also for the manufacturer.

The patient has the advantage of being able to use and to purchase, if required, a single product—i.e. the central unit—which carries out four functions: questionnaire, spirometer, pulse oximeter and activity monitor or motion detector. Furthermore, as an alternative, he/she can also reduce the number of sensors depending on his/her specific diagnostic or therapeutic requirements. Then later on if the requirements change, additional sensors can be purchased without the needing of substitute the central unit.

Having a single central unit which is able to manage and to integrate with every sensor within the system guarantees a major simplicity of use as well as an economic advantage, and the device fully respects the recommendations of the international guide lines for the management of chronic respiratory disease.

The manufacturer has the advantage of manufacturing a single product which can include one or more sensors, according to the needs of the customer. This will reduce the production costs and also optimize the level of stock required to be held, given that only one instead of three different devices needs to be manufactured.

In more detail, the respiratory measurement head through the associated conjugate connector with conjugate contact elements, which then connects to the central unit, represents a very innovative technology and simplifies the use for the patient.

For instance, during the walking test to measure the pulse oximetry and the movement, it is very convenient to reduce the size of the device to be carried by removing the respiratory measurement head and thus facilitate walking. The same advantage is also available when measuring overnight pulse oximetry, when the patient is connected to the device worn on the belt.

All of these aspects improve the use of the device and enable multiple devices to be incorporated into a single system able to carry out a multitude of fundamental diagnostic tests, vital for the home management of chronic respiratory disease.

So to summarize, the integration into a single device of three different sensors for spirometry, pulse oximetry and for motion analysis and of the derived index which compares the desaturation with the movement, completely and totally follows the recommendations of the latest guide lines of the major Scientific Societies for the home management of patients with chronic respiratory disease.

So the very significant strength of this new invention is the real application of these guide lines using a single and simple to use device.

LIST OF REFERENCE USED IN DRAWINGS (1) central unit
(2) Bluetooth module
(3) USB port for data transmission
(4) external power supply
(5) speaker for audio feedback
(6) test report output
(7) flow and volume sensor
(8) pulse oximetry finger sensor
(9) oximetry sensor male connector
(10) oximetry sensor female connector
(11) touch screen display
(12) flow and volume sensor female conjugated connector
(13) central unit male, conjugated connector.

The invention claimed is:

1. A portable device for monitoring and reporting of medical information for and evidence-based management of patients with chronic respiratory disease, said portable device comprising:

a central unit which measures, collects, and stores information related to a state of health of the patient;

a removable sensor for the measurement of respiratory air flow and volume with a connector;

a removable pulse oximetry sensor;

a motion sensor and detector; and a measuring device adapted to measure simultaneously a parameter called oxygen saturation, % $SpO_2$ (pulse oximetry) as well as a physical activity of the patient or accelerometry, wherein the central unit is configured to calculate, during an initial, single 6-minute walking test (6MWT) without giving any supplement of oxygen, an O2 (L/min) representing a quantity of oxygen expressed in L/min which must be given to the patient in order that the patient is able to complete a further 6-minute walking test (6MWT) without desaturating below a level of 90% SpO2, said central unit configured to show said O2 (L/min) on a display at the end of the single 6-minute walking test, wherein when the patient has a base SpO2% at rest below 82% prior to the start of the initial single 6-minute walking test, a supplement of 6 L/min of oxygen must be given in order that the patient is able to complete the test, and wherein the initial single 6-minute walking test has a duration up to six minutes, wherein said O2 (L/min) is calculated by using the following equation:

$$\begin{cases} \text{If } MT \geq 1, \text{ then:} \\ O2(L/\text{min}) = \dfrac{\left\{ \dfrac{\left[ \dfrac{(AUCgap/MT)+}{(BaseSPO2gap/7)} \right]^2 + \sqrt{RT}}{\sqrt{PPD}} - 9.31 \right\}}{8.94} \\ \text{If } MT = 0, \text{ then:} \\ O2(L/\text{min}) = 6 \end{cases}$$

where:

AUCgap represents a difference between an area under a curve where SpO2%=100% vs. time and an area below a curve showing the SpO2% vs. time of the patient during the test;

MT represents a test duration expressed in minutes from a minimum of 0 to a maximum of 6;

BaseSpO2gap represents a difference between SpO2%=100% and an SpO2% baseline at rest before a start of the walk phase of the single 6-minute walking test (6MWT);

RT represents a recovery time in seconds of the patient at the end of said test, for the SpO2 value to return to a base value recorded before the test, even if the test is stopped before the full 6 minutes;

PPD represents a percent predicted distance, which is a percentage of a distance covered by the patient during said test compared to a distance covered by a normal subject.

2. The portable device according to claim 1, wherein the central unit comprises a microprocessor for collecting and storing information and further comprises a wireless or cable transmission device configured to deliver the collected and stored information related to the patient through landline, broadband, wireless and cell-phone technology, wherein the information is received by a web server accessible by medical staff.

3. The portable device according to claim 1, further comprising at least one of an input and output touch screen display, a USB communication port, a Bluetooth or a wireless communication device.

4. The portable device according to claim 1, wherein said motion sensor and detector comprises motion detectors and activity monitors for evaluation of a daily activity of the patient in any setting.

5. The portable device according to claim 4, wherein said motion sensor and detector comprises a triaxial accelerometer for activity monitoring, that is configured to discriminate between low, moderate and high overall activity levels, and to categorize individuals as sedentary, moderately active or active, and the motion sensor and detector is also configured to detect a variety of body positions and physical activities; an output of the accelerometer being measured in the three dimensions—X=anteroposterior, Y=vertical, Z=mediolateral vectors—and being then integrated by the central unit to represent movement as velocity over time using a square root of a sum of squares of each individual vector.

6. The portable device according to claim 5, wherein said central unit comprises a microprocessor operatively connected to a memory and the triaxial accelerometer, wherein the triaxial accelerometer is configured to detect and record a number of aces and the physical activity in each of the three directions, configured to determine and record a position of the body during sleep: face up, face down, right side or left side etc., and configured to measure the movements during the initial single 6-minute walking test.

7. The portable device according to claim 6, wherein said microprocessor and said memory are adapted for linking a level of fall of the % $SpO_2$ or desaturation during sleep, and any rapid desaturation caused by sleep apnea, to the body position, wherein minimum periods during sleeping hours when the patient stands up or walks are identified as waking hours and thus excluded from analysis during sleep.

8. The portable device according to claim 1, wherein the collecting and storing information relating to the patient comprise the acquisition of physiologic measurements or the distance walked and a reduction of the oxygen level in the blood during the exercise.

9. The portable device according to claim 1, wherein the central unit comprises an electrical and mechanical connection assembly connected to the removable sensor for the measurement of respiratory air flow and volume, thereby that when spirometry testing is not required the portable device is absolutely and completely operational for providing other functions to the user.

10. The portable device according to claim 9, wherein the removable sensor and the central unit are configured to perform spirometry tests to determine spirometry parameters including PEF, FEV1, or FEF25%-75% when the removable sensor is connected to the central unit through the electrical and mechanical connection assembly, thereby, wherein the central unit is configured to display results and compare the results to reference values which have been set by a doctor during the portable device setup, at the end of the spirometry test, and further provide to the patient suitable various messages about his/her state of health.

11. The portable device according to claim 1, wherein the central unit is configured to be placed within a belt worn close to the body on a waist, wrist or ankle of the patient, the portable device further comprising a finger probe removably connected to the central unit and configured to measure the % $SpO_2$ and a Pulse Rate (BPM),
wherein the measurement is carried out at rest, or during physical exercise or overnight during sleep,
wherein the motion sensor and detector is a triaxial accelerometer integrated into the central unit.

12. The portable device according to claim 1, further comprising a transmitter of the collected data of the patient to a web server so that said data can then be seen by a doctor.

13. A method of operating the portable device according to claim 1 for the analysis of the initial single six minute walk test (6MWT), said portable device being provided with the central unit that calculates for the O2 (L/min) representing the quantity of oxygen expressed in L/min which must be given to the patient in order that the patient can complete the further 6-minute walking test without desaturating below the level of 90% $SpO_2$, the method comprising at least one the following clinical applications:
calculating an oxygen requirement during exercise using the initial single 6-minute walking test (6MWT) for the prescription of long term oxygen therapy (LTOT);
calculating the oxygen requirement using the initial single 6-minute walking test (6MWT) in the field of rehabilitation therapy; and
calculating a severity of a lung disease, COPD, pulmonary fibrosis and other respiratory conditions, and for treatments of pulmonary conditions using the initial single 6-minute walking test (6MWT) for calculation of a disease prognosis in a patient and for evaluation of results of a course of therapy in the patient.

14. A portable device for monitoring and reporting of medical information for and evidence-based management of patients with chronic respiratory disease, said portable device comprising:
a central unit which measures, collects, and stores information related to a state of health of the patient;
a removable sensor for the measurement of respiratory air flow and volume with a connector;
a removable pulse oximetry sensor;
a motion sensor and detector; and
a measuring device adapted to measure simultaneously a parameter called oxygen saturation, % $SpO_2$ (pulse oximetry) as well as a physical activity of the patient or accelerometry,
wherein the central unit is configured to calculate, during an initial, single 6-minute walking test (6MWT) without giving any supplement of oxygen, an O2 (L/min) representing a quantity of oxygen expressed in L/min which must be given to the patient in order that the patient is able to complete a further 6-minute walking test (6MWT) without desaturating below a level of 90% SpO2, said central unit configured to show said O2 (L/min) on a display at the end of the single 6-minute walking test,
wherein when the patient has a base SpO2% at rest below 82% prior to the start of the initial single 6-minute walking test, a supplement of 6 L/min of oxygen must be given in order that the patient is able to complete the test, and wherein the initial single 6-minute walking test has a duration up to six minutes wherein said motion sensor and detector comprises motion detectors and activity monitors for evaluation of a daily activity of the patient in any setting, wherein said motion sensor and detector comprises a triaxial accelerometer for activity monitoring, that is configured to discriminate between low, moderate and high overall activity levels, and to categorize individuals as sedentary, moderately active or active, and the motion sensor and detector is also configured to detect a variety of body positions and physical activities: an output of the accelerometer being measured in the three dimensions—X=anteroposterior, Y=vertical, Z=mediolateral vectors—and being then integrated by the central unit to represent movement as velocity over time using a square root of a sum of squares of each individual vector, wherein the central unit is adapted to calculate a Desaturation Area and Movement index and to store and show the Desaturation Area and Movement index on a display at the end of the initial single 6-minute walking test;

said Desaturation Area and Movement index representing the area under a % $SpO_2$ curve, including a first portion showing a baseline value at rest of the % $SpO_2$ value and a second portion showing a graph of the % $SpO_2$ when the patient is walking during the initial single 6-minute walking test, obtained in relation to the movement represented by the number of steps taken recorded by the accelerometer during the time the patient is walking during the initial single 6-minute walking test.

* * * * *